United States Patent

Kelada

[11] Patent Number: 5,965,450
[45] Date of Patent: Oct. 12, 1999

[54] IRRADIATION-DISTILLATION APPARATUS AND METHOD FOR MEASURING CYANIDE SPECIES

[76] Inventor: Nabih P. Kelada, 609 Midway Park, Glen Ellyn, Ill. 60137-4228

[21] Appl. No.: 09/109,644

[22] Filed: Jul. 2, 1998

[51] Int. Cl.[6] .......................... G01N 21/75; G01N 33/00
[52] U.S. Cl. ............................ 436/109; 436/52; 436/53; 436/119; 422/81; 422/82
[58] Field of Search .................................. 436/106, 109, 436/119, 52, 53; 422/81, 82

[56] References Cited

U.S. PATENT DOCUMENTS

| | | | |
|---|---|---|---|
| 3,028,224 | 4/1962 | Ferrari, Jr. | 436/109 X |
| 4,265,857 | 5/1981 | Kelada et al. | 422/101 |
| 4,804,631 | 2/1989 | Lue-Hing et al. | 436/109 |

FOREIGN PATENT DOCUMENTS

| | | |
|---|---|---|
| 4233566 | 3/1994 | Germany . |
| 59-30062 | 2/1984 | Japan ..................................... 436/109 |
| 9533203 | 12/1995 | WIPO . |

OTHER PUBLICATIONS

B.K. Afghan et al, *Advances Automat. Anal.* 1970, vol. 2, 291–297.

P.D. Goulden et al. *Anal. Chem.* 1972, 44, 1845–1849.

Z. Zhu et al. *Anal. Chim. Acta* 1987, 198, 25–36.

R. Prober et al, in "Adv. Autom. Anal., Technicon Int. Congr." 7th, 1977, vol. 2, pp. 57–60, Mediad Inc. Tarrytown, N.Y.

J.C.L. Meeussen et al, *Analyst* 1989, 114, 959–963.

N.P. Kelada *J.–Water Pollut. Control Fed.* 1989, 61, 350–356.

N.P. Kelada et al, "Randol Gold Forum" 1992, pp. 385–393, Randol Int.; Golden, Colorado.

J.C.L. Meeussen et al, *Analyst* 1992, 117, 1009–1012.

*Primary Examiner*—Arlen Soderquist
*Attorney, Agent, or Firm*—Ayman M. Nasr

[57] ABSTRACT

A system for measuring the amount of cyanide species in a sample, namely total cyanide, dissociable cyanide, complex cyanide and thiocyanate, by using a single apparatus for simultaneous ultraviolet irradiation and distillation. The system which can be used with either segmented flow or flow injection sampling utilizes filter components which pass only lower frequency ultraviolet radiation interposed between a photoillumination source and the alkaline or acidified sample to first breakdown the strong complex cyanide from the sample without dissociation of thiocyanates. The system then distills the irradiated sample in the same apparatus by utilizing heat emitted from the photoillumination source to recover the total cyanides for measurement. Dissociable cyanides, as well as thiocyanate, are measured using the same apparatus by altering the filter components.

13 Claims, 3 Drawing Sheets

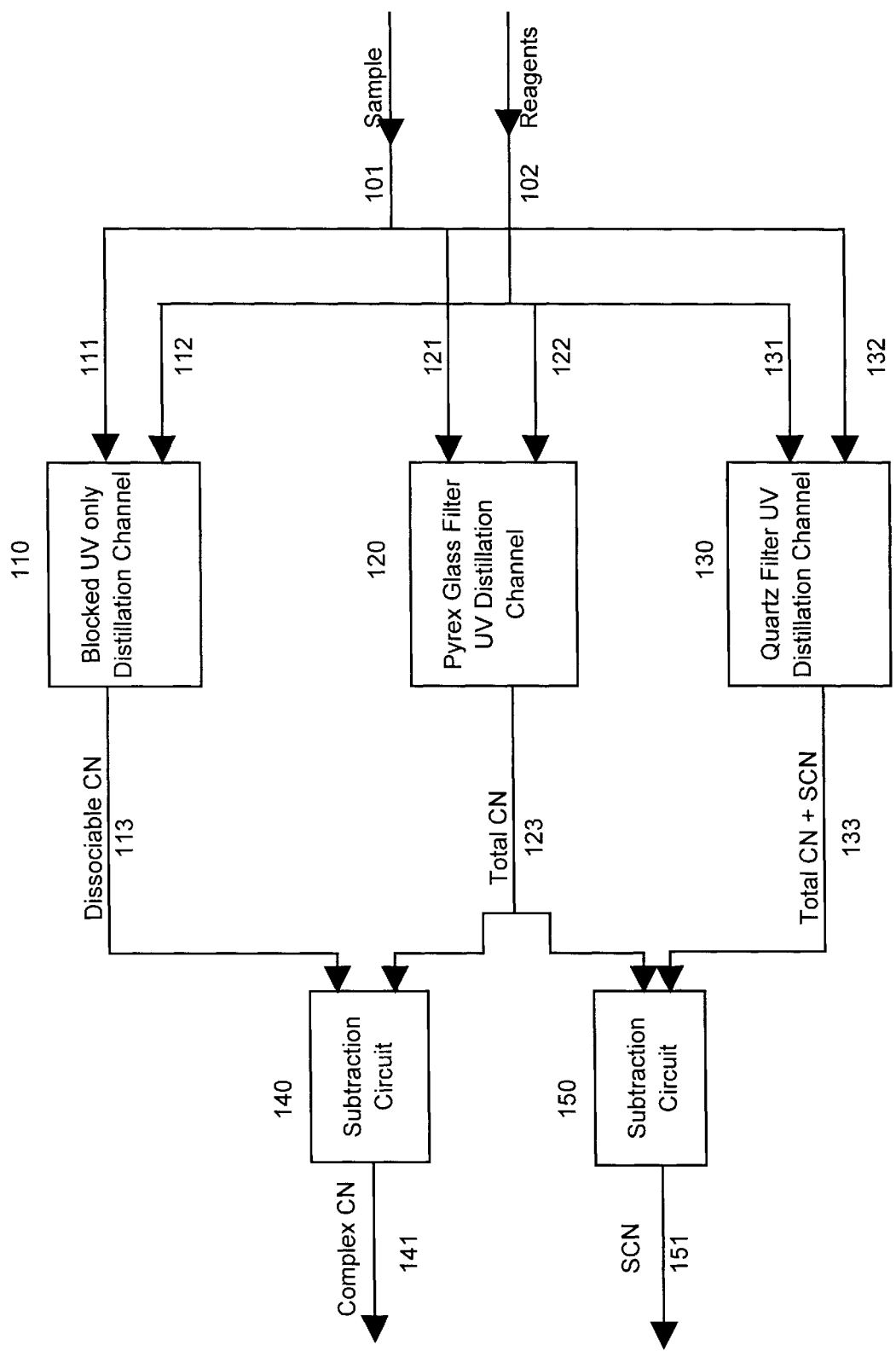
FIG. 5 - Three-Channel Cyanide System

IRRADIATION-DISTILLATION APPARATUS AND METHOD FOR MEASURING CYANIDE SPECIES

TECHNICAL FIELD

This invention relates to an apparatus and method for measuring the cyanide species in a sample. More specifically, it relates to such a single unit for simultaneous photo irradiation and distillation, and has improved capabilities for separation and distinction of different cyanide species, namely, dissociable cyanide, total cyanide, complex cyanide, and thiocyanate. This is in addition to having improved methodology and capability to minimize several problem interferences and to produce accurate and reliable cyanide measurements.

BACKGROUND ART

Cyanides are known to be harmful to our environment and toxic to man and more so to aquatic life. The cyanide compounds are produced and introduced to our environment in many damaging ways. Free cyanide is a highly toxic chemical that is found in the environment at low concentrations coming from natural sources. It reaches toxic levels mostly through industrial processes such as mineral processing, electroplating, and papermaking. The Resource Conservation and Recovery Act ban on land disposal of solid waste containing cyanides poses a major waste management problem for industries using cyanide in their processes.

Cyanide is also a regulatory target because of it toxicity, incompatibility with most publicly owned treatment plants, and danger to sewer workers and marine life. The EPA has imposed limits on the quantity of cyanide in both the treated wastewater that is discharged to sewers and rivers and on any residuals from metal finishing operations (sludges, filters, filter cakes, spent solutions, etc.). A variety of electroplating and metal finishing waste streams contain metal-cyanide complexes. Metal cyanide complexes formed in these industries include metals such as iron, nickel, zinc, cobalt, cadmium, copper, mercury, and precious metals (silver, gold, and platinum).

There is some free cyanide found in electroplating wastewater from cyanide-based plating chemistries; it is one of the most toxic contaminants in the wastewater. Evaporation, while effective, has high energy costs. The commonly used cyanide destruction techniques, such as treatment with oxidizers, do not easily destroy all the cyanide. For example, iron, cobalt, and nickel cyanides are not affected by basic hypochlorite treatment and are often precipitated out into sludge that is formed under the process. Thus, elevated levels of complexed cyanide typically appear in hydroxide-precipitated, heavy metal sludges produced during the treatment of many electroplating wastewater solutions. Waste and wastewater having highly toxic forms of cyanide should be detoxified to a level acceptable to the environment.

Speciation and measurement of the different forms of cyanides are very important to understand the levels to toxicity of each species and offer important steps to protect and improve our environment. Of the various analytical methodology and equipment employed to measure cyanides, automated equipment have achieved more notable results. For example, refer to U.S. Pat. No. 4,265,857 "In-Line Distillation System" and U.S. Pat. No. 4,804,631 "Method and Apparatus for Measuring Cyanide", and to a publication entitled "Chemistry of Wastewater Technology" published by Ann Arbor Science Publishers Inc., of Ann Arbor, Mich., Library of Congress Catalog Card No. 76-50991, ISBN0250, 40185-1, and to a paper by N. P. Kelada entitled "Automated Direct Measurements of Total Cyanide Species and Thiocyanate, and Their Distribution in Wastewater and Sludge", published in the Journal of the Water Pollution Control Federation, Volume 61, No. 3, March 1989, which are incorporated herein by reference.

As described in Chapter 2 of "Chemistry of Wastewater Technology" and in the paper of WPCF Journal such an automated system involves the steps of separation, absorption, and measurement, with ultraviolet irradiation being employed to dissociate complex cyanides in the process of separation, along with thin film distillation and chemical absorption techniques.

A conventional UV irradiation unit includes a UV mercury lamp surrounded by a quartz coil, through which the sample to be tested is passed. The quartz coil is permeable to substantially all of the UV spectrum (approximately 150 to 400 nanometers) enabling the UV radiation to break down the cyanide strong complexes including iron and cobalt cyano complexes. The cobalt very strong complex absorption bands are around 255 and 310 nanometers. However, unwanted thiocyanate (SCN) is also dissociated and detected along with the cyanides.

In advanced UV irradiation units a filtering device is interposed between the UV lamp and the sample to be tested, for passing only the lower frequency UV radiation (longer than 290 nm) for breaking cyanide complexes, while blocking high frequency to inhibit the dissociation of thiocyanate. The "in-line distillation system", or rather thin film distillation, separates the resulting hydrogen cyanide from the acidified sample, and the HCN gas is then absorbed in a sodium hydroxide and recovered for subsequent calorimetric measurement. Thus all of the cyanides can be detected and measured in a large number of samples using an automated segmented flow system.

The above cyanide measuring system, though acceptable for several applications, is cumbersome and has some complicated modules for irradiation separate from the fragile thin film distillation. Additionally, excessive heating and samples containing high gas content could interrupt the complicated waste system, which disrupt the continuous operation causing the loss of many samples and results. In addition, this thin film distillation use is limited to segmented flow systems. More importantly, the previous system does not distinguish all the cyanide species, in particular the dissociable cyanide and the complex cyanide, and is liable to many interferences.

It would be highly desirable to have an improved analytical system that can distinguish between the different cyanide species and can directly measure the dissociable cyanide separately from the total cyanides. It would be beneficial to have a simpler, more rigid apparatus combining both irradiation and distillation in one unit that would not be liable to interruption by high gaseous content of samples. It would also be advantageous if the new technique could operate with either segmented flow or flow injection systems.

DISCLOSURE OF INVENTION

Therefore, the principal object of my invention is to provide a new and improved measurement method and apparatus for cyanide speciation, in the presence of thiocyanate and other interferences, and to indicate separately and accurately the amounts of total cyanide, dissociable cyanide, complex cyanide, and thiocyanate.

Dissociable cyanide includes free cyanide as cyanide ion, CN—, and hydrogen cyanide, HCN, as well as weak metal-cyano-complexes such as those of cadmium and manganese. Iron complexes are not included.

Total cyanide includes all the dissociable cyanide and the strong metal-cyano-complexes such as ferrocyanide, ferricyanide, hexacyanocobaltate, and those of gold and platinum.

Complex cyanide, i.e. strong cyanide complexes such as those of iron and cobalt, are determined by subtraction Complex cyanide=Total Cyanide–Dissociable cyanide Thiocyanate is also determined by the difference of the total cyanide plus thiocyanate measurement (Quartz UV irradiation) and total cyanide (Glass UV irradiation)

Thiocyanate=(Total Cyanide plus Thiocyanate)–Total Cyanide.

The most important object of this invention is to provide a new improved apparatus combining the photo irradiation process simultaneously with the distillation process in a single enclosed rigid unit.

Another object of the present invention is to provide such an improved method and apparatus that can be utilized with either a segmented flow or a continuous flow injection systems as well as other automated measurement techniques such as electrochemical, conductivity, specific ion electrodes, and chromatographic techniques.

An additional object of this invention is to reduce the residence time that the sample to be tested remains in the system and to increase the sampling rate over conventional systems that use a separate thin film distillation unit. This provides improved treatment of problem interferences and satisfactory tolerance of high concentrations of interferences, such as oxidants, aldehydes, and nitrites/nitrates in addition to allowing the results for all parameters to be received simultaneously.

Yet another advantage of this invention is to achieve stronger and more complete distillation in order to give efficient cyanide recovery especially in total cyanide.

The system includes an enclosed irradiation/distillation unit that comprises several components including an ultraviolet lamp for UV radiation to break down the strong cyanide complexes, and the system also utilizes the heat energy emitted from the lamp for distillation. Two sample coils are disposed around the UV lamp in succession, the first "irradiation coil" is basically to receive the specific filtered UV radiation, and the second "distillation coil" is much smaller and closer to the lamp and is mainly for absorbing the heat emitted by the lamp for distillation.

Enclosing the unit also provides an added measure of safety protection for the operator over prior systems employing a separate thin-film distillation unit. In prior systems the waste trap of the thin film distillation may release toxic gases when the samples contain high volatile components, whereas under the present invention, all components are enclosed and waste is released through pump line to a sodium hydroxide absorbing solution before being disposed.

The system includes a cooling fan with variable speed to provide proper sample flow for efficient irradiation and sufficient heat for distillation to give accurate and reproducible cyanide recovery. The size and dimensions and the material characteristics of these sample coils and the layout and design of this irradiation distillation unit allow the utilization of segmented flow or flow injection systems.

The system provides controls and flexibility to change the range of UV irradiation, temperature, and pH during irradiation and distillation to be suitable for the intended cyanide species. The system is also capable of automated addition of specific reagents for treatment of some problem interferences, such as those of thiocyanate, nitrate-nitrite, aldehydes, and oxidants. In this manner, this new and improved method and apparatus accurately measures the intended cyanide species.

Further objects and advantages of my invention will become apparent from a consideration of the ensuing drawings and description.

BRIEF DESCRIPTION OF DRAWINGS

The above and other objects and features of this invention and the manner of attaining them will become apparent, and the invention itself will be best understood by reference to the following description of an embodiment of the invention taken in conjunction with the accompanying drawings, wherein:

FIG. 5—Block Diagram of a Three Channel System for Cyanide Species and Thiocyanate Measurements

BEST MODE FOR CARRYING OUT THE INVENTION

Figure 1:
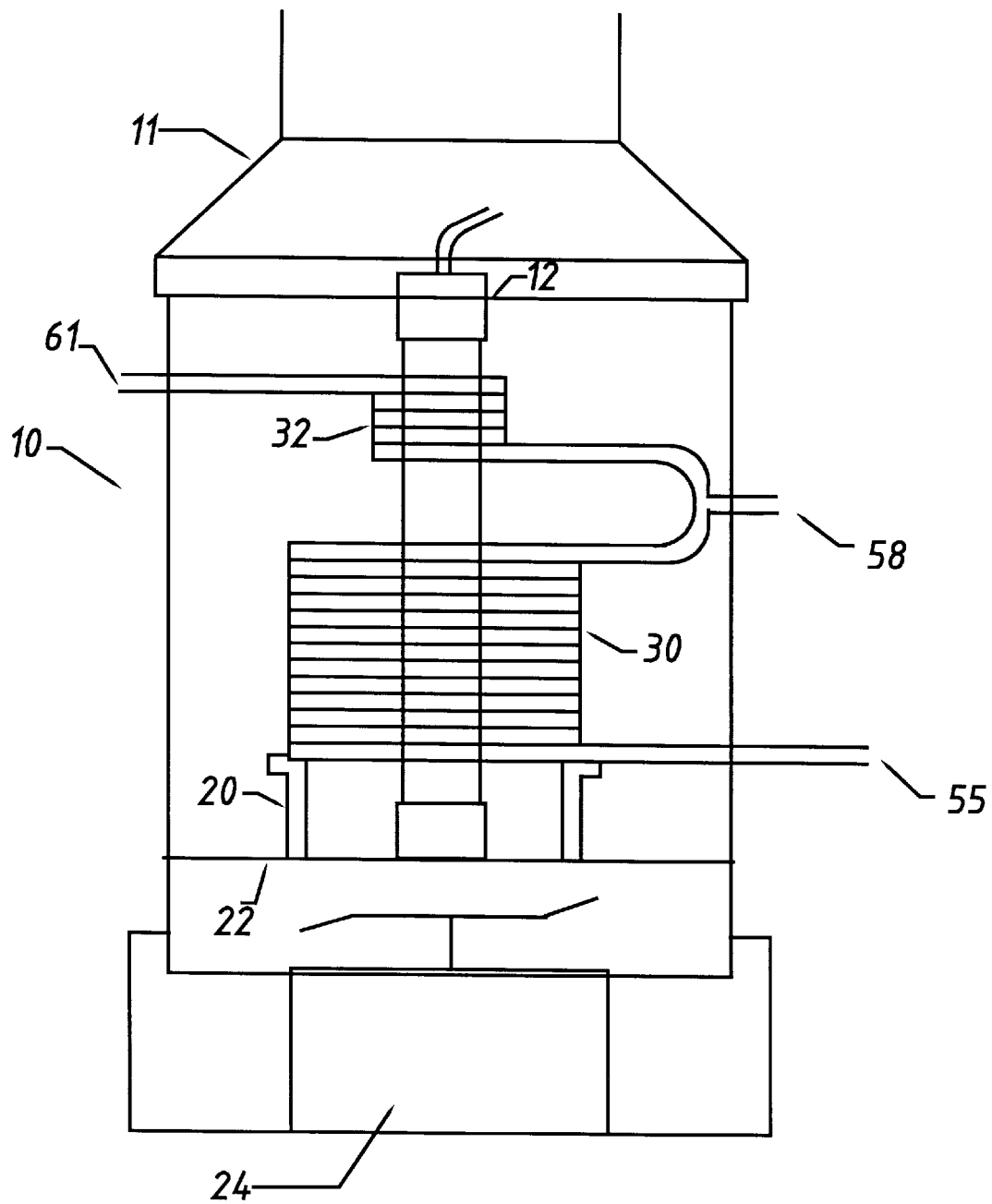
FIG. 1—Diagram of the UV Irradiation/Distillation Apparatus.

Referring to the drawings, FIG. 1 illustrates the construction of the UV irradiation /distillation apparatus 10. FIG. 1 shows a metal housing 11 confines and covers therein a vertically disposed mercury lamp 12 for emitting a full spectrum of ultraviolet, UV, radiation. Two sample coils 30 and 32 are serially connected and disposed around the UV mercury lamp 12. The irradiation coil 30 has an inlet 55 to receive the sample to be tested. Irradiation coil 30 is longer and possesses a wider coil diameter than the distillation coil 32. Irradiation coil 30 is located in close proximity to a cooling fan 24 mounted below the mercury lamp 12. A screen 22 is located below the lamp 12 and above the cooling fan 24 and supports a plurality of rods 20 which in turn support irradiation coil 30 and distillation coil 32. The distillation coil 32 possesses an outlet 61 through which the irradiated and distilled sample exits the apparatus. Distillation coil 32 is shorter and possesses a narrower coil diameter than distillation coil 30 and closely surrounds the upper portion of the lamp 12. The internal diameters of both the irradiation coil tube 30 and distillation coil tube 32 are approximately 1 to 2 mm for use with flow injection sampling systems. For segmented flow systems, the inside diameter of irradiation coil tube 30 and distillation coil tube 32 is approximately 2.5 to 3 mm. The coils are transparent to longer UV range, 290–400 nm, for total cyanide and usually made from Pyrex glass. For thiocyanate analyses, coils 30 and 32 are made from Quartz tubing, and are transparent to all UV range, 200–400 nm. Cooling fan 24 is located below the lamp 12 and is fitted with a variable speed control to optimize the temperature of the irradiation and distillation process.

Figure 2:
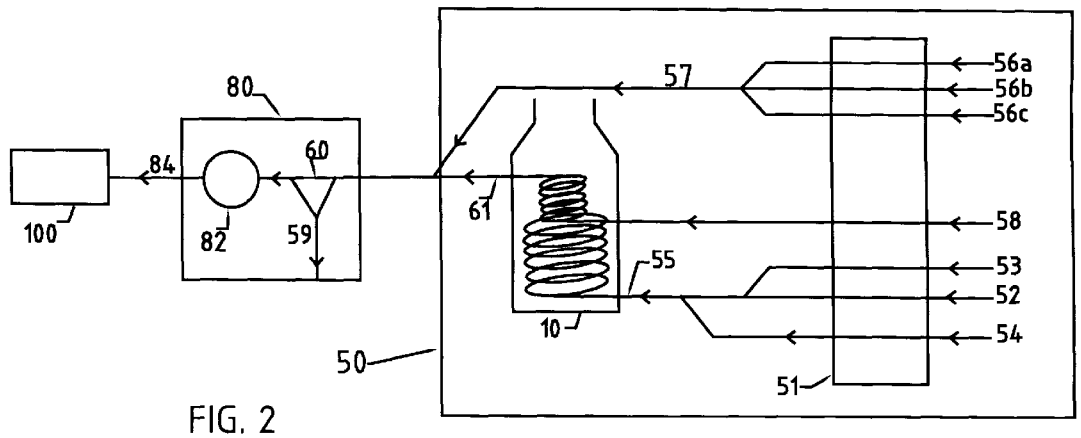
FIG. 2—Schematic Flow Diagram for Cyanide Measuring System.

Referring to the operation of the whole system, and in particular FIG. 2, a schematic flow diagram for a cyanide measuring system constructed according to the present invention is shown. The automated system generally comprises a separation section 50, a recovery section 80, and a measurement section 100. The system is used to measure the different cyanide species contained in a succession of preserved water samples introduced serially to the separation section 50 by a pump 51, through inlet 52. The air for a segmented flow system is introduced through input 53, whereas for flow injection system no air is introduced. A diluent such as water, diluted sodium hydroxide or sodium boron hydroxide, is introduced via line 54 to decrease matrix interferences thereby improving cyanide recovery. The reagents are added through inputs 56-a, 56-b, and 56-c. The sample mixed with the reagents flows through the UV irradiation/distillation apparatus 10. For total cyanide, the flow is directed first through the Pyrex glass irradiation coil 30, thus the UV lamp 12 radiation is filtered and only the wavelengths longer than 290 nm are allowed for irradiation, causing the breakdown and dissociation of cyanide complexes, but not thiocyanate.

A specified acid mixture reagent acidifies the sample stream through inlet 58 before the sample enters the distillation coil 32, which is smaller and narrower and more closely surrounds the upper portion of the lamp 12 than irradiation coil 30. The absorbed heat emitted from the lamp causes evaporation of the samples and the release of hydrogen cyanide gas, HCN. The evaporated samples, flowing continuously from outlet 61 of the UV irradiation distillation unit 10, are mixed with cold water for condensation, as well as air under pressure received via line 57 for air stripping, and the added air acts also as a carrier gas. A debubbler separator 60 then receives all components of this stream. The condensed portion goes to waste via pump tube 59, and the volatile components, hydrogen cyanide gas, HCN, and some water vapor are driven to the recovery section 80. The HCN reacts with sodium hydroxide in the absorption coil 82, and thus the cyanide is recovered.

The outlet of the recovery section is pumped via a line 84 to the measuring section 100. Details of measuring steps are in previous publications and not mentioned here. For calorimetric determination, reagents are added properly to the recovered sample stream and the intensity of the color formed is quantitatively proportional to total recovered cyanide, and is measured by the colorimeter at a wavelength of 870 nm. The colorimeter provides a recordable signal indicative of the recovered cyanide quantity to a recorder and data system.

The system is also capable of tolerating several interferences, such as nitrite/nitrate, aldehydes, and oxidants, and offers better effective treatment for these interferences. The addition of the sodium boron hydride (NaBH4) to the sample stream presents a good treatment for both aldehydes and oxidants. Addition of sulfamic acid is very effective for treating nitrite/nitrate interferences, however this should be done in an acidic medium.

Figure 3:
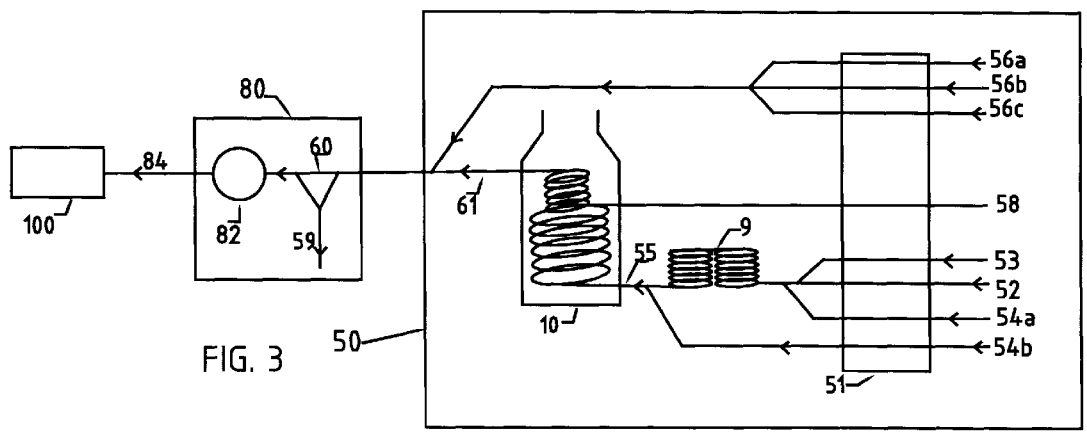
FIG. 3—Manifold for Treatment of Interferences with Alkaline UV Irradiation.

Referring to FIG. 3, the sample is introduced into the system via inlet line 52 where sulfamic acid is added to the sample via inlet line 54-a. The sample, along with the sulfamic acid, enters a long mixing coil 9 in which the sample and sulfamic acid react. Air can also be added via inlet 53 for segmented flow systems. NaBH4 alkaline solution is added through inlet line 54-b to change the pH to alkaline medium (for UV irradiation to break all the strong cyanide complexes, including that of cobalt). The sample then enters the irradiation coil 30 of the UV irradiation-distillation unit 10. The sample is again acidified through inlet line 58 prior to entering distillation coil 32. In this method of treatment, complex cyanide recovery is achieved in the presence of up to 1000 mg/L nitrite, (1 g/L).

Acidification could also be made before entering unit 10 for irradiation, with phosphoric and hypophosphorous and sulfamic acids mixture which is more effective in eliminating nitrite/nitrate interferences. Complete cyanide recovery can be achieved in the presence of more than 10,000-mg/L nitrite (10 g/L). The strong iron ion cyanide complexes are completely recovered, with some decrease in the recovery of cobalt complexes.

Thiocyanate could be somewhat invariably detected when subjected to a long time in acidic condition and heat. Presently, though, this irradiation is acidic, thiocyanate is not detected because of the high speed operation.

Another channel in the automated system is for thiocyanate determination. The system is as previously presented in FIG. 2, except that the irradiation sample coil 30 is made from quartz therefore the full UV range is irradiating the sample (200–400 nm), thus all cyanide complexes as well as thiocyanate are dissociated and included in the measurement.

Figure 4:
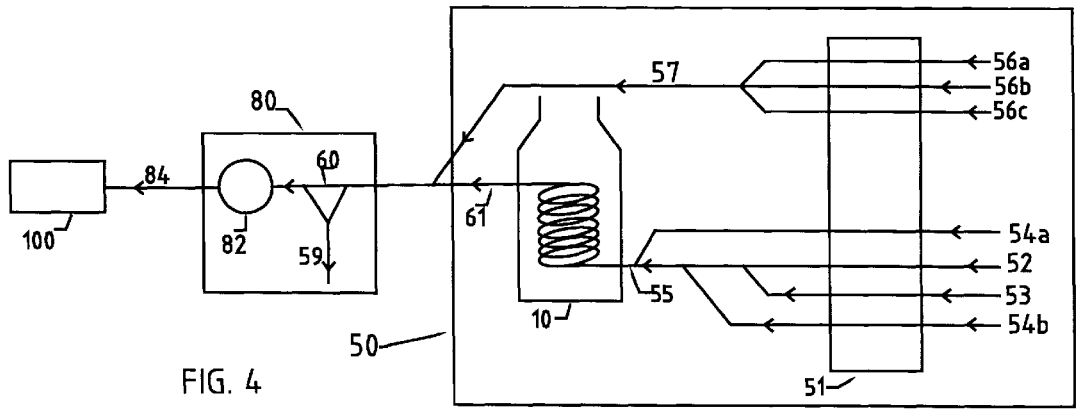
FIG. 4—Manifold for Treatment of Interferences with Acidic UV Irradiation.

For treatment of interferences with acidic UV irradiation, referring to FIG. 4, the sample to be tested is introduced via inlet line 52. NaBH4 is added to the sample stream 54b for treatment of oxidant and aldehyde interferences. Acidification of the sample stream is made before UV irradiation through inlet line 54a with an acid mixture containing sulfamic acid for treatment of nitrite/nitrate interferences. Air can be pumped into the system via line 53 for segmented flow systems. FIG. 4 shows an alternate embodiment using a single coil having a diameter which allows irradiation and distillation to occur simultaneously.

The final measurement signal is indicative of all total cyanide plus thiocyanate, and the difference between this measurement and the total cyanide measurement is the thiocyanate result of the tested sample, as shown in FIG. 5.

A system for dissociable cyanide or rather a third channel, includes only a small opaque distillation coil, blocking the entire UV spectrum, but absorbs the radiated heat for distillation, and directly provides only the dissociable cyanide measurement in the test sample. NaBH4 is added to the sample stream for treatment of aldehyde and oxidant interferences.

FIG. 5 shows a block diagram of a three-channel system for identification and quantification of the intended cyanide species; namely total cyanide, complex cyanide, dissociable cyanide, as well as thiocyanate. In the first channel 110, an opaque small distillation coil is provided to block the whole UV spectrum providing only the dissociable cyanide.

The second channel 120 includes a Pyrex glass system that is permeable only to UV wavelengths longer than 290 nm to provide output signals indicative of the complete total cyanide.

In the third channel 130 a quartz irradiation coil permeable to the full spectrum of UV irradiation 200–400 nm is provided thereby dissociating all of the cyanides and all thiocyanate, to provide a signal indicative of the complete cyanides plus all thiocyanate together in the same sample.

Therefore the signal 141 is the difference between the two measurements of channels 110 and 120, namely the Pyrex glass channel for total cyanide and only distillation channel for dissociable cyanide, and provides an indication of the complex cyanide contained in each sample under test.

Total cyanide−Dissociable cyanide=complex cyanide

Also, the signal 151 is the difference between the two measurements made by channels 120 and 130, and provides an indication of the thiocyanate contained in each sample.

(Total cyanide plus Thiocyanate)−Total cyanide=Thiocyanate

I claim:

1. A system for measuring total cyanide, dissociable cyanide, and complex cyanide in a sample comprising:

photoillumination means for irradiating the sample and dissociating cyanides contained therein;

means to carry the sample located adjacent the photoillumination means having an irradiation section configured to allow radiation from the photoillumination means to cause dissociation of cyanides in the sample and a distillation section configured for distilling dissociated cyanides in the sample by heat generated by the photoillumination means, said irradiation section and said distillation section being connected in series;

means for acidifying the sample connected to the means to carry the sample;

means to inhibit thiocyanate dissociation located between said photoillumination means and said means to carry the sample; and measuring means for recovering cyanide and generating a recordable signal indicative of the amount of cyanide in the sample, said measuring means connected to the means to carry the sample.

2. The system as recited in claim 1 wherein said photoillumination means includes an ultraviolet light.

3. The system as recited in claim 1 wherein the means to carry the sample is a tube having a predetermined inside diameter;

in the irradiation section the tube is in the shape of a coil disposed around the photoillumination means and having a first coil diameter; and in the distillation section the tube is in the shape of a coil disposed around the photoillumination means and having a second coil diameter smaller than the first coil diameter.

4. The system as recited in claim 3 wherein the inside diameter of the tube is dimensioned to permit segmented flow or flow injection of the sample through the tube.

5. The system recited in claim 1 further comprising a speed controllable cooling fan to optimize the temperature of the system to regulate the flow of the sample thereby allowing irradiation to be achieved before distillation.

6. A system for measuring total cyanide, dissociable cyanide, and complex cyanide in a sample comprising:

an ultraviolet photoillumination means for irradiating the sample and dissociating cyanides contained therein;

means to carry the sample including a coil disposed around said photoillumination means to simultaneously allow irradiation and distillation of the sample by the photoillumination means;

means for acidifying the sample connected to the means to carry the sample;

means to inhibit thiocyanate dissociation located between said photoillumination means and said means to carry the sample; and measuring means for recovering cyanide and generating a recordable signal indicative of the amount of cyanide in the sample, said measuring means connected to the means to carry the sample.

7. The system as recited in claim 6 wherein the inside diameter of the tube is dimensioned to permit segmented flow or flow injection of the sample through the tube.

8. A system for measuring dissociable cyanide in a sample comprising:

a photoillumination means and a distillation coil disposed around the photoillumination means for distilling dissociable cyanides in the sample by heat generated by the photoillumination means, wherein the distillation coil is opaque to radiation that would cause complex cyanides to dissociate;

means for acidifying the sample connected to the distillation coil; and measuring means for recovering cyanide and generating a recordable signal indicative of the amount of cyanide in the sample, said measuring means connected to the distillation coil.

9. A method for measuring total cyanide in a preserved alkaline sample, comprising the steps of:

irradiating the sample with filtered ultraviolet light from a photoillumination source to dissociate complex cyanides in the sample while inhibiting thiocyanate dissociation;

acidifying the irradiated sample;

heating the sample with heat from the photoillumination source to elevate the temperature of the sample for distillation thereby causing separation of hydrogen cyanide in the sample;

recovering the separated hydrogen cyanide; and measuring the recovered hydrogen cyanide to generate a recordable signal indicative of the quantity of total cyanide species in the sample.

10. The method of claim 9, further comprising measuring thiocyanate in the sample, comprising the steps of:

irradiating the sample with unfiltered ultraviolet light from the photoillumination source to dissociate complex cyanides and thiocyanate in the sample;

distilling, recovering and measuring hydrogen cyanide to generate a recordable signal indicative of the quantity of total cyanide species and thiocyanate in the sample;

subtracting the total cyanide signal to generate a signal indicative of thiocyanate in the sample.

11. A method for measuring total cyanide in a sample, comprising the steps of:

acidifying the sample;

irradiating the sample with filtered ultraviolet light from a photoillumination source to dissociate complex cyanides in the sample while inhibiting thiocyanate dissociation;

heating the sample with heat from the photoillumination source to elevate the temperature of the sample for distillation thereby causing separation of hydrogen cyanide in the sample;

recovering the separated hydrogen cyanide; and measuring the recovered hydrogen cyanide to generate a recordable signal indicative of the quantity of total cyanide species in the sample.

12. A method for measuring dissociable cyanide in a sample, comprising the steps of:

acidifying the sample;

passing the sample through an opaque distillation coil;

heating the sample in the coil with heat from an ultraviolet photoillumination source to elevate the temperature of the sample for distillation thereby causing separation of hydrogen cyanide in the sample;

recovering the separated hydrogen cyanide; and measuring the recovered cyanide to generate a recordable signal indicative of the quantity of dissociable cyanide in the sample.

13. The method of claim 12, further comprising measuring complex cyanide in the sample, comprising the steps of:

irradiating the sample with filtered ultraviolet light from the photoillumination source to dissociate complex cyanides in the sample;

distilling, recovering and measuring hydrogen cyanide to generate a recordable signal indicative of the quantity of total cyanide species in the sample;

subtracting the dissociable cyanide signal from the total cyanide signal to generate a signal indicative of complex cyanides in the sample.

* * * * *